United States Patent [19]

Felix et al.

[11] Patent Number: 4,959,352

[45] Date of Patent: Sep. 25, 1990

[54] CYCLIC GROWTH HORMONE RELEASING FACTOR ANALOGS AND METHOD FOR THE MANUFACTURE THEREOF

[75] Inventors: Arthur M. Felix, West Caldwell; Edgar P. Heimer, Sparta, both of N.J.

[73] Assignee: Hoffmann-La Roche Inc., Nutley, N.J.

[21] Appl. No.: 399,123

[22] Filed: Aug. 28, 1989

Related U.S. Application Data

[63] Continuation of Ser. No. 98,340, Sep. 18, 1987, abandoned.

[51] Int. Cl.$^5$ .................. A61K 37/02; C07K 7/54
[52] U.S. Cl. ........................ 514/9; 530/317; 530/321; 514/11
[58] Field of Search .............. 530/317, 321; 514/9, 514/11

[56] References Cited

U.S. PATENT DOCUMENTS

4,774,319  9/1988  Ono et al. .................. 530/324

FOREIGN PATENT DOCUMENTS

136475A2  4/1985  European Pat. Off.
188214A2  7/1986  European Pat. Off.

OTHER PUBLICATIONS

Heimer et al., J. Cell Biochem Suppl. O(12 Part B) 1988.
Hruby, Life Sciences, vol. 31, pp. 189–199, (1982).
Blakiston's Gould Medical Dictionary 3rd Ed. Osol (ed.) McGraw-Hill Book Co. pp. 1127–1128 (1972).
Durieux et al., Peptides, Structure and Function; Proceedings of the Ninth American peptide Symposium pp. 575–578 (1985).
Felix et al., Int. J. Peptide Protein Res. 32, pp. 441–454 (1988).
Veber et al., Nature, vol. 292, pp. 55–58 (1981).
Kessler et al., J. Am. Chem. Soc. vol. 105, pp. 6944–6952 (1983) Campbell, J. Animal Sci., 67, Suppl. 1, (1989).
Campbell et al., J. Animal Sci., 66, Suppl. 1, p. 291 (1988).
Mowles et al., Endocrinologia Japonica, vol. 34, Suppl. 1, p. 148 (1987).
Felix et al., Peptides=Chemistry, Structure and Biology.
(River et al., ed). pp. 226–228, 1990. (Proceedings of the Eleventh American Peptide Symposium (Jul. 9–14, 1989).

*Primary Examiner*—Lester L. Lee
*Assistant Examiner*—Christina Chan
*Attorney, Agent, or Firm*—George M. Gould; William H. Epstein; Patricia S. Rocha

[57] ABSTRACT

Linear and cyclic Growth Hormone Releasing Factor Analogs and a method for stimulating the release of Growth Hormone in subjects by administering to the subject an effective amount of the compounds of the invention.

14 Claims, No Drawings

CYCLIC GROWTH HORMONE RELEASING FACTOR ANALOGS AND METHOD FOR THE MANUFACTURE THEREOF

This application is a continuation of application Ser. No. 07/098,340, filed Sept. 18, 1987, now abandoned.

Growth in animals is believed to be regulated by a cascade of bio-regulatory molecules. The hypothalamus produces a substance called Growth Hormone Releasing Factor (GRF) which in turn acts upon the pituitary to cause release of growth hormone. The pituitary is maintained under negative feedback control by somatostatin and insulin growth factor (IGF). GRF has been found to be enormously active, and capable of stimulating the release of microgram per ml. levels of growth hormone in the blood. GRF can be utilized therapeutically in most of the areas now considered candidates for treatment by growth hormone, for example treatment of pituitary dwarfism, diabetes resulting from growth hormone production, enhancement of wound healing, treatment of burns, or retardation of the aging process.

The successful isolation of GRF was due partly to the discovery that pancreatic tumors associated with acromegaly ectopically produced large quantities of GRF. Three forms of GRF, consisting of peptides homologous from the amino-terminus of 44, 40, and 37 amino acids, were isolated.

The 44 amino acid amidated form of GRF is considered to be the parent molecule. A wide variety of synthetic analogs have been produced. They consist of the original polypeptide or biologically active fragments thereof which exhibit various amino acid substitutions. The changes have been specifically engineered to often yield synthetic analogs with biological properties superior to those of the parent molecule. Accordingly, the desire has been to engineer GRF analogs which exhibit maximum biological activity in terms of potency, effectiveness, and stability, for example.

To date, all of the known GRF analogs are of linear configuration. Generally, linear peptides are very flexible molecules and lack a well-defined conformation. Each amino acid in a linear peptide is exposed to the surrounding milieu resulting in greater susceptibility to enzymatic and chemical degradation.

A cyclic peptide (lactam) is a peptide wherein the side-chain carboxy terminus of an acidic amino acid (e.g. Asp or Glu) is attached to the side-chain amino terminus of a basic amino acid (e.g. Lys). The resultant peptide chain formed via the generation of an amide bond. The bonding between the two peptides in the chain yields a ring (or lactam) structure.

The biological properties of cyclic peptides are often altered relative to those of their linear analogs. Cyclic peptides are much more rigid with well-defined shapes and interior amino acid residues which are shielded from the surrounding milieu. These changes are reflected in the biological properties of the peptide. The cyclic peptides' duration of action will be longer since the compact structure renders it less susceptible to chemical and enzymatic degradation. The bioavailability of the cyclic peptide will be increased due to changes in the tissue distribution caused by the shielded interior amino acid residues. Further, the well defined conformation of the cyclic peptide will give it greater specificity for the target receptor thus reducing the probability of undesirable biological activities concomitant with the desired one. In contrast with linear peptides there are generally both central and peripheral receptors for a given linear peptide, and there is considerable cross reactivity of a given peptide with receptors for another peptide.

SUMMARY OF THE INVENTION

The instant invention is directed to linear and cyclic analogs of GRF of the specific amino acid sequence set forth herein including the pharmaceutically acceptable salts thereof.

The instant invention is also directed to a method of stimulating the release of growth hormone in a subject by administering to the subject an effective amount of the compounds of the invention.

The following symbols and terminology as utilized in this specification shall be defined as follows:

1. cyclic peptide - or lactam means a peptide wherein the side-chain carboxy terminus of an acidic amino acid (e.g. Asp or Glu) is attached to the side-chain. amino terminus of a basic amino acid (e.g. Lys) The resultant peptide chain is formed via the generation of an amide bond (lactam).

means that the eighth amino acid or cyclo$^{8.12}$ "A" in the peptide chain is attached to the twelfth amino acid "B" in the chain to yield a cyclic lactam structure.

3. GRF means human growth hormone releasing factor which is a polypeptide having the amino acid sequence H—Tyr—Ala—Asp—Ala—Ile—Phe—Thr—Asn—Ser—

—Tyr—Arg—Lys—Val—Leu—Gly—Gln—Leu—Ser—Ala—

—Arg—Lys—Leu—Leu—Gln—Asp—Ile—Met—Ser—

—Arg—Gln—Gln—Gly—Glu—Ser—Asn—Gln—Glu—Arg—

—Gly—Ala—Arg—Ala—Arg—Leu—NH$_2$;

or biologically active fragments thereof having at least the first 28 amino acids of the full polypeptide and displacing growth hormone releasing activity.

4. [Leu$^{27}$]GRF means a polypeptide having an amino acid sequence corresponding to GRF in which a leucine residue has been substituted fo methionine at position 27. Analogs of GRF are generally indicated by setting forth the substituted amino acid in brackets before GRF.

5. GRF (1-29) means a fragment of the GRF peptide having the first 29 amino acids of the full sequence. In general, numbers in parenthesis following GRF indicate fragments of the full GRF polypeptide.

6. des NH$_2$Tyr$^1$ means that the amino terminal NH$_2$ group is removed from the Tyrosine residue at position 1.

DETAILED DESCRIPTION

The instant invention comprises cyclic peptides of the formula

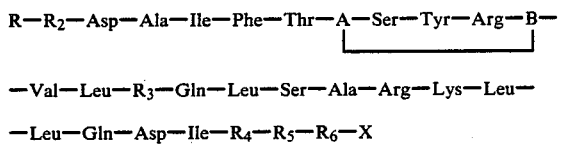
                                                                                                I.

wherein
R=Tyr, desNH$_2$-Tyr, Ac-Tyr. His, or N-Methyl-L-Tyr
R$_2$=Ala, or D-Ala, N-methyl-D-Ala
R$_3$=Gly, Ala, Leu, Val, Ile, Nle, NVal, β-Ala, or α-Aib
R$_4$=Met, Leu, Nle, Ile
R$_5$=Ser, or Asn
R$_6$=an amino acid sequence selected from the group consisting of Arg-Gln-Gln-Gly-Glu-Ser-Asn-Gln-Glu-Arg-Gly-Ala-Arg-Ala-Arg-Leu or fragments thereof where the fragment is reduced in number by 1 to 15 amino acids from the carboxyl end
X=OH, NH$_2$,

where R$_7$ and R$_8$ are each independently lower alkyl
A=Asp, Glu, α-aminoadipic acid, or α-aminopimelic acid
B=Lys, Orn, diaminopropionic acid, diaminobutyric acid or the pharmaceutically acceptable salts; and the side chain carboxy terminus of A is bonded in an amide bond to the side chain amino terminus of B.

Preferred are peptides of Formula I wherein R=Tyr, desNH$_2$-Tyr; N-methyl-L-Tyr R$_2$=Ala, D-Ala; R$_3$=Ala; and X=NH$_2$ Further preferred is a Formula I peptide as above wherein A=Asp; B=Lys (and the side-chain carboxy terminus of Asp is covalently linked to the side-chain amino terminus of Lys as an amide bond); R$_4$=Met; R$_5$=Ser; and R$_6$=Arg.

Particularly preferred is a peptide wherein R=N-methyl-L-Tyr (N-meTyr) and R$_2$=Ala, said peptide having the formula:

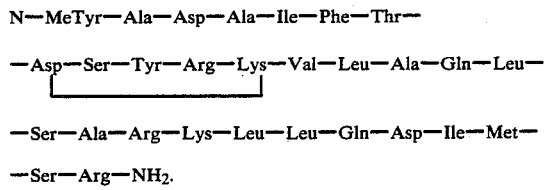

Also particularly preferred is a peptide wherein R=N-MeTyr and R$_2$=D-Ala said compound having the formula:

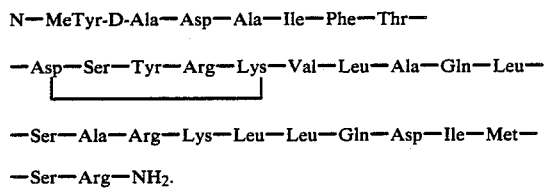

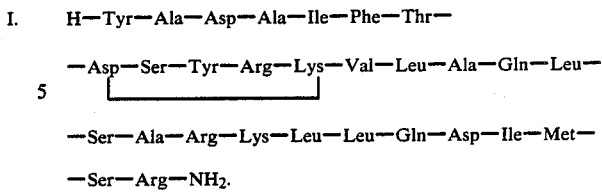

Also particularly preferred is wherein R$_2$=D-Ala said peptide having the formula

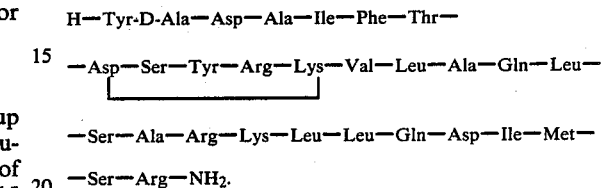

Also preferred is a Formula I compound wherein R=des NH$_2$Tyr.

Particularly preferred is wherein R$_2$=Ala said peptide having the formula

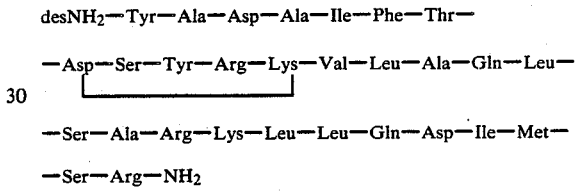

Also particularly preferred is wherein R=D-Ala said peptide having the formula

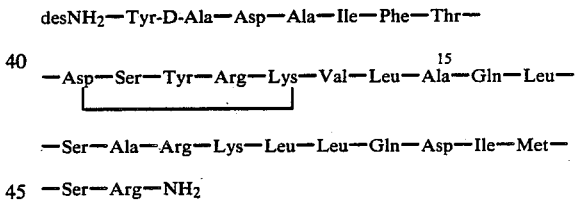

The instant invention also comprises linear peptides of the above set forth amino acid sequences.

The peptides are synthesized by a suitable method such as by exclusive solid phase synthesis, partial solid phase methods, by fragment condensation or by classical solution synthesis. Recombinant DNA techniques can also be used for those analogs containing only natural amino acid residues. The peptides are preferably prepared by solid phase peptide synthesis as described by Merrifield, J. Am. Chem. Soc. 85, 2149 (1963). The synthesis is carried out with amino acids that are protected at the alpha-amino-terminus. Trifunctional amino acids with labile side-chains are also protected with suitable groups which will prevent a chemical reaction from occurring at that site during the assemblage of the peptide. The alpha-amino protecting group is selectively removed to allow subsequent coupling reactions to take place at the amino-terminus. The conditions for the removal of the alpha-amino protecting group do not cause deprotection of the side-chain protecting groups.

The alpha-amino protecting groups are those known to be useful in the art of stepwise synthesis of peptides.

Included are acyl type protecting groups (e.g. formyl, trifluoroacetyl, acetyl), aromatic urethane type protecting groups (e.g. benzyloxycarbonyl (Cbz) and substituted benzyloxycarbonyl). aliphatic urethane protecting groups (e.g. t-butyloxycarbonyl (Boc), isopropyloxycarbonyl, cyclohexyloxycarbonyl) and alkyl type protecting groups (e.g. benzyl, triphenylmethyl). The preferred protecting group is Boc. The side-chain protecting groups for Tyr include tetrahydropyranyl, tert.-butyl, trityl. benzyl, Cbz, 4-Br-Cbz and 2,6-dichlorobenzyl. The preferred side-chain protecting group for Tyr is 2,6-dichlorobenzyl. The side-chain protecting groups for Asp include benzyl, 2,6-dichlorobenzyl, methyl, ethyl and cyclohexyl. The preferred side-chain protecting group for Asp is cyclohexyl. The side-chain protecting groups for Thr and Ser include acetyl, benzoyl, trityl, tetrahydropyranyl, benzyl, 2,6-dichlorobenzyl and Cbz. The preferred protection group for Thr and Ser is benzyl. The side-chain protecting groups for Arg include nitro, Tos, Cbz. adamantyloxycarbonyl or Boc. The preferred protecting group for Arg is Tos. The side-chain amino group of Lys may be protected with Cbz, 2-Cl-Cbz, Tos or Boc. The 2-Cl-Cbz is the preferred protecting group for Lys. The selection of the side-chain protecting groups is based on the following: The side-chain protecting group remains intact during coupling and is not split off during the deprotection of the amino-terminus protecting group or during coupling conditions. The side-chain protecting group must be removable upon the completion of the synthesis of the final peptide and using reaction conditions that will not alter the target peptide.

Solid phase synthesis is usually carried out from the carboxy-terminus by coupling the alpha-amino protected (side-chain protected) amino acid to a suitable solid support. An ester linkage is formed when the attachment is made to a chloromethylated or hydroxymethyl resin and the resultant target peptide will have a free carboxyl group at the C-terminus. Alternatively, a benzhydrylamine or p-methylbenzhydrylamine resin is used in which case an amide bond is formed and the resultant target peptide will have a carboxamide group .at the C-terminus. These resins are commercially available and their preparation is described by Stewart et al., "Solid phase peptide Synthesis" (2nd Edition, pierce Chemical Co., Rockford, Ill., 1984).

The C-terminal amino acid, Arg, protected at the side-chain with Tos and at the alpha-amino function with Boc is coupled to the benzhydrylamine resin using various activating agents including dicyclohexylcarbodiimide (DCC), N,N'-diisopropylcarbodiimide or carbonyldiimidazole. Following the attachment to the resin support the alpha-amino protecting group is removed by using trifluoroacetic acid (TFA) or HCl in dioxane at a temperature between 0° and 25° . Dimethylsulfide is added to the TFA after the introduction of methionine (Met) to suppress possible S-alkylation. After removal of the alpha-amino protecting group the remaining protected amino acids are coupled stepwise in the required order to obtain the desired peptide sequence. Various activating agents can be used for the coupling reactions including DCC, N,N'-diisopropylcarbodiimide, benzotriazol-1-yl-oxy-tris-(dimethylamino)phosphonium hexafluorophosphate (BOP) and DCC-hydroxybenzotriazole (HOBt). Each protected amino acid is used in excess (>2.5 equivalents) and the couplings are usually carried out in DMF, CH$_2$Cl$_2$ or mixtures thereof. The extent of completion of the coupling reaction is monitored at each stage by the ninhydrin reaction as described by Kaiser et al., Anal. Biochem., 34, 595 (1970). In cases where incomplete coupling is determined the coupling reaction is repeated. The coupling reactions can be performed automatically on a Vega 250, Applied Biosystems synthesizer or other commercially available instrument. After the entire assemblage of the target peptide the peptide-resin is deprotected with TFA/dithioethane and then reacted with a reagent such as liquid HF for 1-2 hours at 0° which cleaves the peptide from the resin and removes all side-chain protecting groups.

Side-chain to side-chain cyclization on the solid support requires the use of an orthogonal protection scheme which enables selective cleavage of the side-chain functions of acidic amino acids (e.g. Asp) and the basic amino acid (e.g. Lys). The 9-fluorenylmethyl (OFm) protecting group for the side-chain of Asp and the 9-fluorenylmethoxycarbonyl (Fmoc) protecting group for the side-chain of Lys can be used for this purpose. In these cases the side-chain protecting groups (OFm and Fmoc) of the Boc-protected peptide-resin are selectively removed with piperidine in DMF. Cyclization is achieved on the solid support using various activating agents including DCC, DCC/HOBt or BOP. The HF reaction is carried out on the cyclized peptide-resin as described above.

Purification of the polypeptides of the invention can be effected using procedures well known in peptide chemistry. The subject polypeptides may be purified using preparative hplc; however, other known chromatographic procedures such as gel permeation, ion exchange and partition chromatography or countercurrent distribution can also be employed.

The instant invention also comprises a method of stimulating the release of Growth Hormone in a subject by administering to the subject an effective amount of the Formula I peptides.

The polypeptides of this invention have growth hormone compositions in accordance releasing activity. pharmaceutical with the invention include analogs of about 29 to 44 amino acids in length, or a nontoxic salt of any of these, dispersed in a pharmaceutically or.veterinarily acceptable liquid or solid carrier. Such pharmaceutical compositions can be used for therapeutic or diagnostic purposes in clinical medicine, both human and veterinary. For example, they are useful in the treatment of growth-related disorders such as hypopituitary dwarfism and diabetes resulting from abnormalities in growth hormone production. Furthermore, they can also be used to stimulate the growth or enhance feed efficiency of animals raised for meat production, to enhance milk production and stimulate egg production.

Appropriate dosages of the polypeptides of the invention to be administered will vary somewhat depending on the individual subject and the condition being treated. The skilled worker will be able to determine appropriate dosages based on the known circulating levels of growth hormone associated with normal growth and the growth hormone releasing activity of the polypeptide.

As is well known in the art, treatment of growth-related disorders will necessitate varying dosages from individual to individual depending upon the degree of insufficiency of growth hormone production. Generally, a dosage range of from 0.04 µg/kg/day to about 20.0 µg/kg/day based on body weight of the subject may be used to stimulate release of growth hormone. The dosages employed to stimulate growth activity in livestock will be significantly higher (per kg. of subject weight) than the dosages employed to restore normal growth in cases of growth hormone deficiencies such as pituitary dwarfism in humans. In livestock generally a dosage in the range of from 0.4 µg/kg/day to about 100 µg/kg/day subcutaneously may be used to stimulate release of pituitary growth hormone.

Thus, there is provided in accordance with this invention a method of treating growth-related disorders characterized by insufficient production of growth hormone which comprises administering.an amount of the analogs of this invention sufficient to stimulate the production of growth hormone to levels associated with normal growth.

Normal levels of growth hormone vary considerably among individuals and, for any given individual, levels of circulating growth hormone vary considerably during the course of a day. In adult humans, normal serum levels of growth hormone have been reported to vary from about 0-10 nanograms/ml. In children, normal serum levels of growth hormone have been reported to vary from about 0-20 nanograms/ml.

In order to treat hypopituitary dwarfism effectively with the described analogs, treatment is administered during the period of normal growth. In females, this period generally does not extend far beyond the onset of menses. Thus, treatment of females should be effected approximately from the age of 12 to 16 years, depending upon the individual. In males. the stimulation of growth may be possible for a considerably longer period of time beyond puberty. Thus, effective treatment of males will normally be possible up to about 18 to 19 years of age and, in some individual cases, up to about 25 years.

There is also provided a method of increasing the growth rate of animals by administering an amount of the analog sufficient to stimulate the production of growth hormone at a level greate than that associated with normal growth.

The polypeptides of the invention can be administered in the form of human or veterinary pharmaceutical compositions which can be prepared by conventional pharmaceutical formulation techniques. Compositions suitable for oral, or parenteral administration may be employed. A suitable dosage form for pharmaceutical use is from about 0.01 to about 0.5 mg of the compound of the invention, which may by lyophilized for reconstitution with sterile water or saline. The composition should be maintained at a pH below about 5.0 in order to maintain the stability of the analog. Serum albumin from the species being treated (e.g. human serum albumin in the case of humans, bovine serum albumin in the case of cows and so forth) may also be present together with other known pharmaceutical adjuvants.

The present invention will be described in connection with the following examples which are set forth for the purposes of illustration only.

EXAMPLE I

Synthesis of Cyclo$^{8,12}$[Ala$^{15}$]-GRF(1–29)-NH$_2$

Preparation of Boc-Aro(Tos)-Benzhydrylamine-resin

Benzhydrylamine-resin (60 g, 0.7 meq/g, 42 meq) was washed with 900 ml each of $CH_2Cl_2$, MeOH, $CH_2Cl_2$, 25% Et3N in $CH_2Cl_2$ (3 times), $CH_2Cl_2$, MeOH and $CH_2Cl_2$ Boc-Arg (Tos)-OH (35.95 g, 84 mmmol, 2 eq) in DMF (80 ml)-$CH_2Cl_{12}$ (600 ml) was added, shaken for 5 min and DCC (17.3 g, 84 mmol, 2 eq) added and reacted for 24 hours. The resultant Boc-Arg (Tos)-BHA-resin was washed with DMF, $CH_2Cl_2$, MeOH and $CH_2Cl_{12}$ Amino acid analysis of an aliquot revealed a substirution of 0.38 mmol/g. The resin was acetylated with 300 ml of 50% Ac2O-pyridine for 2h at 25° and washed with $CH_2Cl_2$, MeOH, $CH_2Cl_2$ and dried in vacuo to give 70 g of Boc-Arg(Tos)-BHA-resin (substitution: 0.6 meq/g).

Preparation of [Aso$^8$(OFm),Lys$^{12}$(Fmoc),Ala$^{15}$]-GRF(1–29)-benzhydrylamine-resin The Boc-Arg(Tos)-BHA-resin (70 g, 0.6 meq/g, 42 meq) was deprotected and neutralized according to the protocol described in FIG. 2. Trifunctional amino acids were protected as follows: Boc-Arg(Tos), Boc-Asp(O-cHex), Boc-Glu-(OBzl), BocLys(2Cl-Z), Boc-Ser(Bzl), Boc-Thr(Bzl), Boc-Tyr-(2,6-Cl$_2$Bzl), Boc-Asp$^8$(OFm) and Boc-Lys$^{12}$(Fmoc). Exceptions to the protocol were for the coupling of Boc-Gln-OH (positions 24 and 16) and for the coupling immediately following Gln (positions 23 and 15) in which 3 equiv. of the symmetric anhydride was used in DMF (double coupled). In special cases in which a third coupling was required the HOBt ester was prepared using 2.5 equiv. each of Boc-amino acid, 1-hydroxybenzotriazole and DCC preactivated in DMF (120 ml), filtered (removal of dicyclohexylurea) and dilution with toluene to 1.2 L. Coupling proceeded for 2 hours and 1.5% diisopropylethylamine added and reacted for 15 min. longer.

A portion of intermediate [Ala$^{15}$]-GRF(13–29)-BHA-resin (1.88 g, 0.714 mmol) was removed and stepwise solid phase synthesis continued as described above. After incorporation of Lys$^{12}$(Fmoc), Step 6 was replaced with 0.6% DIEA/CH2C12 The coupling with Boc-Asn-OH (6 equiv.) was carried out by preactivation with 1-hydroxybenzotriazole (6.6 equiv.) and DCC (6 equiv.).

Preparation of Cyclo$^{8,12}$[Ala$^{15}$]-GRF(1–29)-NH$_2$

Following the assemblage of Boc-[Asp$^8$(OFm)-,Lys$^{12}$(Fmoc), Ala$^{15}$]-GRF(1–29)-BHA-resin (2.72 g, 0.714 mmol) the resin was deprotected with 20% piperidine/DMF for 20 min to give Boc-[Asp$^{8,}$Lys$^{1-2}$,Ala$^{15}$]-GRF(1–29)-BHA-resin. A portion (1.40 g, 0.40 mmol) was cyclized by reaction with BOP reagent (443 mg, 1.0 mmol, 2.5 eq) in DMF (40 ml) containing Et$_3$N (157 µL, 1.12 mmol. 2.8 eq) for 4 hours. After washing, cyclization was repeated two more times for 11 hours and 3 hours (negative Kaiser ninhydrin test) and the peptide-resin washed, dried and cleaved with HF (~20 ml) containing DTE (1 ml/g resin) at 0° for 2 hours. Evaporation of HF was followed by washing with EtOAc, extraction with TFA (6×5 ml), evaporation and trituration with ether.

Purification and Characterization of Cyclo$^{8,12}$[Ala$^{14}$]-GRF(1–29)-NH$_2$ The crude product (708 mg) was suspended in 20 ml of H$_2$O (0 025% TFA), stirred, centrifuged, filtered and applied on a Synchropak RP-P column (2.0×50 cm). Eluant (A) H$_2$O (0.025% TFA) - (B) ACN (0.025% TFA); linear gradient 20–45% (B) in 120 min., flow rate 4 ml/min. Fractions were collected at 1 min intervals. Fractions 82–89 were pooled and lyophilized to give 84 mg of semi-pure product. Side-bands were obtained from fractions 90-93 (33 mg). The semi-pure material (84 mg) was repurified on a Nucleosil $C_{18}$ column (1.0×50 cm; 5μ). Eluant (A) $H_2O$ (0.1% TFA) - (B) ACN (0.1% TFA); linear gradient 20-40% (B) in 120 min; flow rate 3 ml/min. Fractions were collected at 1 min. intervals. Fractions 120-121 were pooled and lyophilized to give homogeneous product (9 mg) and fractions 122-138 gave 42 mg of product that was ≧97% pure.

The product was shown to be homogeneous by analytical hplc. Amino acid analysis (6M HCl, 110°, 24h): Asp, 2.72; Thr, 0.96; Ser, 2.98; Glu, 2.14; Ala, 4.00; Val, 0.96; Met, 0.97; Ile, 1.89: Leu, 4.28; Tyr, 2.01; Phe, 0.98; Lys, 2.06; Arg, 3.04.

EXAMPLE 2

Synthesis of Cyclo$^{8,12}$[desNH$_2$Tyr$^1$,D-Ala$^2$,Ala$^{15}$]-GRF(1-29)-NH$_2$ A portion of intermediate [Ala$^{15}$]-GRF(13-29)-BHA-resin (5.1 g, 1.63 mmol) was removed and stepwise solid phase synthesis continued as described above in FIG. 2. After incorporation of Lys$^{12}$(Fmoc), Step 6 was replaced with 0.6% DIEA/CH$_2$Cl$_2$. The synthesis was continued to give 6.4 g of Boc-[Asp$^8$(OFm),Lys$^{12}$(Fmoc),Ala$^{15}$]-GRF(3-29)-BHA-resin. A 1.0 g (0.255 mmol) portion was subjected to 1 cycle of solid phase synthesis with Boc-D-Ala-OH to give Boc-[D-Ala$^{2l}$,Asp$^8$(OFm),Lys$^{12}$(Fmoc),Ala$^{15}$]-GRF(2-29)-BHA-resin. A 0.5 g portion was subjected to a final cycle with desNH$_2$Tyr-OH to give [desNH$_2$Tyr, D-Ala$^2$,Asp$^8$(OFm)-Lys$^{12}$(Fmoc),Ala$^{15}$]-GRF(1-29)-BHA-resin which was deprotected with 20% piperidine/DMF for 20 min and cyclized with BOP reagent (170 mg, 0.384 mmol, 3 eq) in DMF (20 ml) containing DIEA (0.3 ml, 2.2mmol) for 2 hours. The cyclization was repeated With fresh BOP reagent (negative Kaiser ninhydrin test) and the peptide washed, dried and cleaved (as above) with HF (~10 ml) at 0° for 2 hours. Evaporation of HF was followed by washing with EtOAc, extraction with TFA, evaporation and trituration with ether to give 229 mg crude product. purification was carried out by preparative hplc as described above for Cyclo$^{8,}$$^2$[Ala$^{15}$]-GRF(1-29)-NH$_2$.

EXAMPLE 3

Synthesis of Cyclo$^{8,12}$ desNH$_2$Tyr$^1$,Ala$^{15}$]-GRF(1-29)-NH$_2$

A 1.0 g (0.255 mmol) portion of Boc-[Asp$^8$(OFm), Lys$^{12}$(Fmoc),Ala$^{15}$]-GRF(3-29)-BHA-resin was subjected to 2 cycles of solid phase synthesis with Boc-L-Ala-OH followed by desNH$_2$Tyr-OH to give [desNH$_2$Tyr$^1$,Asp$^8$(OFm),Lys$^{12}$ (Fmoc),Ala$^{15}$]-GRF(1-29)-BHA-resin which was deprotected with 20% piperidine/DMF for 20 min and cyclized with BOP reagent (170 mg, 0.384 mmol, 3 eq) in DMF (20 ml) containing DIEA (0.3 ml, 2.2mmol) for 2 hours. The cyclization was repeated with fresh BOP reagent (negative Kaiser ninhydrin test) and the peptide washed, dried and cleaved (as above) with HF (~10 ml) at 0° for 2 hours. Evaporation of HF was followed by washing with EtOAc, extraction with TFA, evaporation and trituration with ether to give 450 mg crude product. purification was carried out by preparative hplc as described above for Cyclo$^{8,12}$-[Ala$^{15}$]-GRF(1-29)-NH$_2$.

EXAMPLE 4

Synthesis of Cyclo$^{8,12}$[D-Ala$^2$,Ala$^{15}$]-GRF(1-29)-NH$_2$

A 0.5 g portion of Boc-[D-Ala$^2$,Asp$^8$(OFm),Lys$^{12}$(Fmoc). Ala$^5$]-GRF(2-29-BHA-resin [from above]was subjected to a final cycle with Boc-Tyr[2,6-Cl$_2$Bzl)-OH to give Boc-[D-Ala$^2$, Asp$^8$(OFm),Lys$^{12}$(Fmoc),Ala$^{15}$]-GRF(1-29)-BHA-resin which was deprotected with 20% piperidine/DMF for 20 min and cyclized with BOP reagent (170 mg, 0.384 mmol, 3 eq) in DMF (20 ml) containing DIEA (0.3 ml, 2.2mmol) for 2 hours. The cyclization was repeated with fresh BOP reagent (negative Kaiser ninhydrin test) and the peptide washed, dried and cleaved (as above) with HF (~10 ml) at 0° for 2 hours. Evaporation of HF was followed by washing with EtOAc, extraction with TFA, evaporation and trituration with ether to give 198 mg crude product. Purification was carried out by preparative hplc as described above for Cyclo$^{8,12}$[Ala$^{15}$]-GRF(1-29)-NH$_2$.

EXAMPLE 5

Synthesis of Cyclo$^{8,12}$ N-Methyl-Tyr$^1$,D-Ala$^2$,Ala$^{15}$]GRF(1-29)-NH$_2$ A 0.5 g portion of Boc-[D-Ala$^2$,Asp$^8$(OFm),Lys$^{12}$(Fmoc), Ala$^{15}$]-GRF(2-29)BHA-resin (from above) was subjected to a final cycle with Boc-N-Methyl-Tyr(2,6-Cl$_2$Bzl)-OH to give Boc-[N-MeTyr(2,6-Cl$_2$Bzl)D-Ala$^2$,Asp$^8$(OFm),Lys$^{12}$(Fmoc),Ala$^{15}$]-GRF(1-29)-BHA-resin which was deprotected with 20% piperidine/DMF for 20 min and cyclized with BOP reagent (170 mg, 0.384 mmol, 3 eq) in DMF (5 ml) containing DIEA (0.103 ml, 0.765 mmol, 6 eq) for 2 hours. The cyclization was repeated 2 more times with fresh BOP reagent (negative ninhydrin test) and the peptide washed, dried and cleaved (as above) with HF (~10 ml) at 0° for 2 hours. Evaporation of HF was followed by washing with EtOAc. extraction with TFA. evaporation and trituration with ether to give 219 mg crude product. purification was carried out by preparative hplc as described above for Cyclo$^{8,12}$[Ala$^{15}$]-GRF(1-29)-NH$_2$.

While the invention has been described in connection with the preferred embodiment, it is not intended to limit the scope of the invention to the particular form set forth, but, on the contrary it is intended to cover such alternatives, modifications, and equivalents as may be included within the spirit and scope of the invention as defined by the appended claims.

We claim:

1. A cyclic peptide of the formula

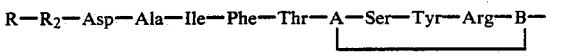

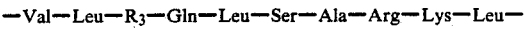

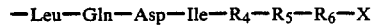

wherein
R=Tyr, desNHhd$_2$-Tyr, Ac-Tyr, His or N-Methyl-L-Tyr
R$_2$=Ala, D-Ala or N-methyl-D-Ala
R$_3$=Gly, Ala, Leu, Val, Ile, Nle, NVal, β-Ala or "a-Aib"
R$_4$=Met, Leu, Nle or Ile
R$_4$=Ser or Asn $R_6$=an amino acid sequence selected from the group consisting of Arg-Gln-Gln-Gly-Glu-Ser-Asn-Gln-Glu-Arg-Gly-Ala-Arg-Ala-Arg-Leu and fragments thereof where the fragment is reduced in number by 1 to 15 amino acids from the carboxyl end

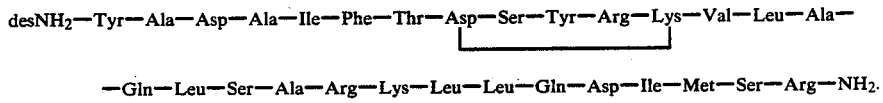

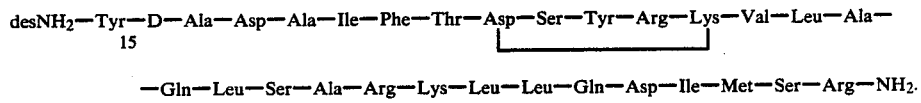

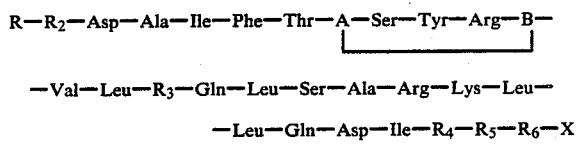

A = Asp, Glu, α-aminopimelic acid or a -aminoadipic acid

B = Lys, Orn, diaminopropionic acid, diaminobutyric acid or a pharamaceutically acceptable salt thereof; and the side chain carboxy terminus of A is bonded via an amide bond to the side chain amino terminus of B.

2. The peptide of claim 1 wherein R=Tyr, desNH$_2$-=Tyr, N-Methyl-L-Tyr; R$_2$=Ala, D-Ala; R$_3$=Ala; and X=NH$_2$.

3. The peptide of claim 2 wherein A=Asp; B=Lys (and the side-chain carboxy terminus of Asp is covalently linked to the side-chain amino terminus of Lys as an amide bond); R$_4$=Met; R$_5$=Ser; and R$_6$=Arg.

4. The peptide of claim 3 wherien R=Tyr.

5. The peptide of claim 4 wherein R$_2$=Ala said compound having the formula:

—Gln—Leu—Ser—Ala—Arg—Lys—Leu—Leu—Gln—Asp—Ile—Met—Ser—Arg—NH$_2$.

6. The compound of claim 4 wherein R$_2$=D-Ala said compound having the formula:

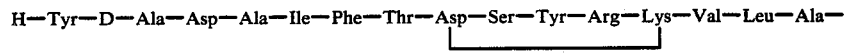

—Gln—Leu—Ser—Ala—Arg—Lys—Leu—Leu—Gln—Asp—Ile—Met—Ser—Arg—NH$_2$.

7. The compound of claim 3 wherein R=desNH$_2$-Tyr.

8. The compound of claim 7 wherein R$_2$=Ala said compound having the formula:

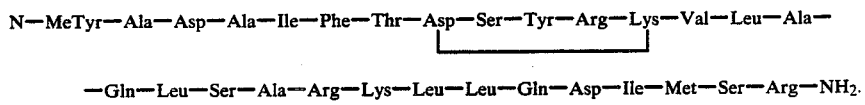

—Gln—Leu—Ser—Ala—Arg—Lys—Leu—Leu—Gln—Asp—Ile—Met—Ser—Arg—NH$_2$.

9. The compound of claim 7 wherein R$_2$=D-Ala said compound having the formula:

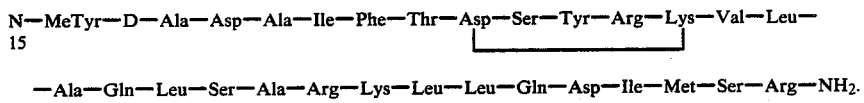

—Gln—Leu—Ser—Ala—Arg—Lys—Leu—Leu—Gln—Asp—Ile—Met—Ser—Arg—NH$_2$.

10. The compound of claim 3 wherein R=N-Methyl-L-Tyr.

11. The compound of claim 10 wherein R$_2$=Ala said compound having the formula:

N—MeTyr—Ala—Asp—Ala—Ile—Phe—Thr—Asp—Ser—Tyr—Arg—Lys—Val—Leu—Ala—

—Gln—Leu—Ser—Ala—Arg—Lys—Leu—Leu—Gln—Asp—Ile—Met—Ser—Arg—NH$_2$.

12. The compound of claim 10 wherein R$_2$=-Ala said compound having the formula:

N—MeTyr—D—Ala—Asp—Ala—Ile—Phe—Thr—Asp—Ser—Tyr—Arg—Lys—Val—Leu—

—Ala—Gln—Leu—Ser—Ala—Arg—Lys—Leu—Leu—Gln—Asp—Ile—Met—Ser—Arg—NH$_2$.

13. A method of stimulating the release of growth hormone in a subject which comprises administering to said subject an effective amount of a cyclic peptide of the formula:

R—R$_2$—Asp—Ala—Ile—Phe—Thr—A—Ser—Tyr—Arg—B—

—Val—Leu—R$_3$—Gln—Leu—Ser—Ala—Arg—Lys—Leu—

—Leu—Gln—Asp—Ile—R$_4$—R$_5$—R$_6$—X wherein

R=Tyr, desNH$_2$-Tyr, Ac-Tyr, His or N-Methyl-L-Tyr

R$_2$=Ala, D-Ala or N-Methyl-D-Ala

R$_3$=Gly, Ala, Leu, Val, Ile, Nle, NVal, β-Ala or α-Aib

R$_4$=Met, Leu, Nle, or Ile

R$_5$=Ser or Asn $R_6$ = an amino acid sequence selected from the group consisting of Arg-Gln-Gln-Gly-Glu-Ser-Asn-Gln-Glu-Arg-Gly-Ala-Arg-Ala-Arg-Leu and fragments thereof where the fragment is reduced in umber by 1 to 15 amino acids from the carboxyl end

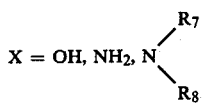

where $R_7$ and $R_8$ are each independently lower alkyl

A = Asp, Glu, α-aminopimelic acid or α-aminoadipic acid

B = Lys, Orn, diaminopropionic acid, diaminobutyric acid or a pharmaceutically acceptable salt thereof.

14. The method of claim 13 wherein the compound is administered orally or parenterally.

* * * * *

UNITED STATES PATENT AND TRADEMARK OFFICE
CERTIFICATE OF CORRECTION

PATENT NO. : 4,959,352

DATED : September 25, 1990

INVENTOR(S) : ARTHUR M. FELIX AND EDGAR P. HEIMER

It is certified that error appears in the above-identified patent and that said Letters Patent is hereby corrected as shown below:

Column 2:

Line 3, "cross reactivity" should be --cross-reactivity--.

Line 20, delete the period after "side-chain."

Line 21, insert a period after "(e.g. Lys)." Also, insert --2.-- aligned with the "1." on line 18.

Line 29, "cyclo$^{8.12}$" should be cyclo$^{8,12}$.

Line 50-51, "displacing" should be --displaying--.

Line 54, "fo" should be --for--.

Line 62, "des NH$_2$Tyr$^1$" should be --desNH$_2$Tyr$^1$--.

UNITED STATES PATENT AND TRADEMARK OFFICE
CERTIFICATE OF CORRECTION

PATENT NO. : 4,959,352

DATED : September 25, 1990

INVENTOR(S) : ARTHUR M. FELIX AND EDGAR P. HEIMER

It is certified that error appears in the above-identified patent and that said Letters Patent is hereby corrected as shown below:

Column 3:

Line 46, "(N-meTyr)" should be --(N-MeTyr)--.

Column 4:

Line 23, "des $NH_2$Tyr" should be --des$NH_2$Tyr--.

Column 5:

Line 45, "pierce" at the end of the line should be --Pierce--.

UNITED STATES PATENT AND TRADEMARK OFFICE
CERTIFICATE OF CORRECTION

PATENT NO. : 4,959,352

DATED : September 25, 1990

INVENTOR(S) : ARTHUR M. FELIX AND EDGAR P. HEIMER

It is certified that error appears in the above-identified patent and that said Letters Patent is hereby corrected as shown below:

Column 6:

Line 1, "couplinq" should be --coupling--.

Lines 39-42 are misprinted and should read --The polypeptides of this invention have growth hormone releasing activity. Pharmaceutical compositions in accordance with the invention include analogs of about --. The text on line 41 should continue on line 40.

UNITED STATES PATENT AND TRADEMARK OFFICE
CERTIFICATE OF CORRECTION

PATENT NO. : 4,959,352

DATED : September 25, 1990

INVENTOR(S) : ARTHUR M. FELIX AND EDGAR P. HEIMER

It is certified that error appears in the above-identified patent and that said Letters Patent is hereby corrected as shown below:

Column 7:

Line 38, "level greate" should be --level greater--.

Line 67, "$CH_2Cl_2Boc$" should be --$CH_2Cl_2 \bullet Boc$--.

Line 68, "-$CH_2Cl_{12}$" should be -- -$CH_2Cl_2$--.

Column 8:

Line 4, "$CH_2Cl_{12}$" should be --$CH_2Cl_2$.--.

Line 5, "substirution" should be --substitution--.

Line 12, "[$Aso^8$(OFm)" should be --[$Asp^8$(OFm)--.

Line 37, "CH2Cl2" should be --$CH_2Cl_2$.--.

UNITED STATES PATENT AND TRADEMARK OFFICE
CERTIFICATE OF CORRECTION

PATENT NO. : 4,959,352

DATED : September 25, 1990

INVENTOR(S) : ARTHUR M. FELIX AND EDGAR P. HEIMER

It is certified that error appears in the above-identified patent and that said Letters Patent is hereby corrected as shown below:

Line 46-47, "$Lys^1$ 2" should be --$Lys^{12}$--.

Line 59, "$Cyclo^{8,12}[Ala^{14}]$" should be --$Cyclo^{8,12}[Ala^{15}]$--.

Column 9:

Line 19, "$desNH_2Tyrl^1$" should be --$desNH_2Tyr^1$--.

Line 29, "$Boc-[D-Ala^2 1$" should be --$Boc-[D-Ala^2,$--.

Line 30, ",$Asp^8(OFm)$," should be --$Asp^8(OFm),$--.

Line 32, "$[desNH_2Tyr,$" should be --$[desNH_2 Tyr^1,$--.

Lines 45-46, "$Cyclo_2^{81}[Ala^{15}]$" should be --$Cyclo^{8,12}[Ala^{15}]$--.

Line 50, insert a bracket (--[--) before the "des."

UNITED STATES PATENT AND TRADEMARK OFFICE
CERTIFICATE OF CORRECTION

PATENT NO. : 4,959,352

DATED : September 25, 1990

INVENTOR(S) : ARTHUR M. FELIX AND EDGAR P. HEIMER

It is certified that error appears in the above-identified patent and that said Letters Patent is hereby corrected as shown below:

Line 55, "[desNH-" should be --[desNH$_2$- --.

Line 56, "$_2$Tyr$^1$" should be --Tyr$^1$--.

Line 66, "purification" should be "Purification."

Column 10:

Line 5, "Ala$^5$" should be --Ala$^{15}$--.

Line 25, "N-Methyl-Tyr1$^1$" should be --[N-Methyl-Tyr$^1$,--.

Line 62, "desNHhd$_2$-Tyr," --desNH$_2$-Tyr--.

Line 66, "a-Aib" should be --$\alpha$-Aib--.

Columns 11 and 12:

The amino acid sequences for claims 5, 6, 8, 9, 11 and 12 should fit directly under the claim, e.g., like claims 1 and 13.

e.g., like claims 1 and 13.

UNITED STATES PATENT AND TRADEMARK OFFICE
CERTIFICATE OF CORRECTION

PATENT NO. : 4,959,352

DATED : September 25, 1990

INVENTOR(S) : ARTHUR M. FELIX AND EDGAR P. HEIMER

It is certified that error appears in the above-identified patent and that said Letters Patent is hereby corrected as shown below:

Column 11:

Line 46, "=Tyr," should be --Tyr--.

Column 12:

Line 29, "$R_2$=-Ala" should be --$R_2$=D-Ala--.

Column 13:

Line 11, "umber" should be --number--.

Signed and Sealed this

Twenty-fifth Day of August, 1992

Attest:

DOUGLAS B. COMER

Attesting Officer     Acting Commissioner of Patents and Trademarks